United States Patent
Oishi et al.

(10) Patent No.: US 7,575,562 B2
(45) Date of Patent: Aug. 18, 2009

(54) BLOOD PURIFICATION DEVICE

(75) Inventors: Takayuki Oishi, Haibara-gun (JP); Yasushi Takakuwa, Haibara-gun (JP)

(73) Assignee: Nikkiso Co., Ltd., Tokyo (JP)

( * ) Notice: Subject to any disclaimer, the term of this patent is extended or adjusted under 35 U.S.C. 154(b) by 0 days.

(21) Appl. No.: 11/235,916

(22) Filed: Sep. 26, 2005

(65) Prior Publication Data

US 2006/0074369 A1    Apr. 6, 2006

(30) Foreign Application Priority Data

Oct. 6, 2004    (JP) .............................. 2004-294106

(51) Int. Cl.
*A61M 37/00*    (2006.01)
*A61M 1/00*    (2006.01)

(52) U.S. Cl. ...................... 604/4.01; 604/5.01; 422/44

(58) Field of Classification Search ............... 604/4, 604/65, 4.01–6.16, 8–10, 28–34; 422/44–48; 210/644–646; 600/485, 495
See application file for complete search history.

(56) References Cited

U.S. PATENT DOCUMENTS

| 4,464,164 | A | * | 8/1984 | Troutner et al. ............ 604/6.05 |
| 4,662,355 | A | * | 5/1987 | Pieronne et al. ............... 600/17 |
| 5,098,373 | A | * | 3/1992 | Polaschegg ................ 604/6.05 |
| 5,368,555 | A | * | 11/1994 | Sussman et al. ............ 604/6.05 |
| 6,090,048 | A | * | 7/2000 | Hertz et al. ................. 600/485 |
| 6,248,087 | B1 | * | 6/2001 | Spears et al. ............... 604/6.14 |
| 2001/0012917 | A1 | | 8/2001 | Inukai | |
| 2002/0193691 | A1 | * | 12/2002 | Sato ........................... 600/495 |

* cited by examiner

*Primary Examiner*—Leslie R Deak
*Assistant Examiner*—Philip R Wiest
(74) *Attorney, Agent, or Firm*—Darby & Darby PC

(57) ABSTRACT

A blood purification device allows controlling a false alarm and allows detecting accurately an abnormality in a patient who is undergoing a blood purification treatment or in the device which is running. The hemodialysis equipment includes blood circuit made of an arterial blood circuit having an arterial needle at its end and a venous blood circuit having a venous needle at its end; a blood pump; a dialyzer purifying the blood flowing in blood circuit; a venous blood pressure sensor which can detect pressure of a patient's blood flowing in the venous blood circuit; a venous blood pressure monitoring means for comparing a base value of the pressure measured by the venous blood pressure sensor or pressure predicted to be measured with a predetermined alarm-threshold. The device also has a venous blood pressure monitoring means allows updating the predetermined alarm threshold at a predetermined period of time.

11 Claims, 4 Drawing Sheets

BLOOD PURIFICATION DEVICE

INCORPORATION BY REFERENCE

The present application claims priority under 35 U.S.C. §119 to Japanese Patent Application No. 2004-294106 filed on Oct. 6, 2004. The content of the application is incorporated herein by reference in its entirety.

FIELD OF THE INVENTION

The present invention relates to a blood purification device which purifies blood from a patient in extracorporeal blood circulation.

BACKGROUND OF THE INVENTION

In general, blood purification treatment such as dialysis treatment, a blood circuit made of flexible tubing is used to place the blood of patient in extracorporeal circulation. This blood circuit arrangement mainly includes an arterial blood circuit having an arterial needle at one end to collect blood from the patient and a venous blood circuit having a venous needle at the other end to return the blood to the patient. A dialyzer between the arterial blood circuit and the venous blood circuit purifies the blood circulating extracorporeally.

Such dialyzer is made of plural hollow fibers inside the dialyzer. Blood flow inside each hollow fiber and dialysate flowing outside the hollow fibers (i.e. between external surface face of the hollow fiber and inside surface face of the dialyzer case). The hollow fiber is a blood purification membrane with small pores on its surface. Wastes in the blood flowing inside the hollow fiber are discharged into the dialysate after passing through the blood purification membrane, and the purified blood returns to the patient.

Meanwhile, the pressure of the patient's blood flowing in the venous blood circuit is monitored during dialysis treatment, and when the pressure is remarkably increased or decreased, it is determined that an abnormality has occurred and that the abnormality is reported to a medical worker by an alarm. Specifically, a pressure sensor connected to a monitoring tube extending from the air-layer side of a venous drip chamber is attached to the venous blood circuit and is used to constantly monitor the blood pressure of the patient's blood flowing in the venous blood circuit. If the measured pressure by the pressure sensor is out of a predetermined range, which is an upper and lower values of an alarm-threshold, the event is alarmed as a possible occurrence of abnormality.

In such a blood purification device, the alarm threshold set at the beginning of the treatment is always constant during the treatment, and when it is reset, the threshold becomes constant. However, there are following issues remained to be solved.

Normally, the venous blood pressure, as shown in FIG. 6, varies depending on the patient's condition during the dialysis treatment. The alarm-threshold, upper value D1 and lower value D2, are set as in FIG. 6 until reset and when the pressure is beyond upper value D1 at T1, an alarm would be activated even though no abnormality has occurred.

When the patient changes sides or position, or a substitution fluid is added to the patient during medical treatment, the venous pressure measured varies and according to such change, an alarm sometimes is activated because the pressure is beyond upper value D1 or lower value D2. Such frequent false alarms produces undue burden on a medical worker.

Upper value D1 and/or lower value D2 are set larger in some medical agency to avoid activating false alarms, so that when an event of abnormality on extracorporeal circuit occurs because of, for example, changes in patient's condition or clogging of the dialyzer, or the needle coming off from the patient or the needle separating from the blood circuit, the changes of venous pressure, which must be unavoidably alarmed, will not be detected. For example, even when the needle comes off from the patient or the needle separates from the blood circuit and the blood pressure is lower than the dotted line in the same figure, the pressure measured does not go beyond lower value D2, and as a result, no alarm is activated.

When the needle comes off, in many cases, the decrease of venous blood pressure is very small even though the flow resistance on introduction of the blood to the patient body is null because some flow resistance is generated by the needle. Such a small decrease can be hardly detected. Therefore a false alarm is frequently activated, making the detection of actual abnormality difficult, the abnormality being related to sudden changes in the patient, the needle coming off from the patient, the needle separating from the blood circuit, or defects of the extracorporeal system.

SUMMARY OF THE INVENTION

The object of the present invention is to eliminate false alarms and provide a blood purification device which accurately detects abnormality in the patient undergoing blood purification treatment and of the device being used.

The present invention provides a blood purification device including a blood circuit having the arterial needle and the venous needle which circulate extracorporeally the blood collected from the patient; a blood pump provided at the arterial blood circuit of the blood circuit; a blood purification means, which is connected between the arterial blood circuit and the venous blood circuit, for purifying the blood flowing in the blood circuit; a venous blood pressure measuring means for measuring the pressure of the patient's blood flowing in the venous blood circuit; and a venous blood pressure monitoring means for activating an alarm when the pressure measured or the pressure predicted to be measured by the venous blood pressure measuring means is out of a predetermined alarm-threshold range by comparing with each other. The venous blood pressure monitoring means updates the predetermined alarm-threshold at a predetermined period of time.

Specifically, the venous blood pressure monitoring means allows controlling an erroneous alarm and accurately detecting an abnormal condition of the patient undergoing a blood purification treatment and the device for the treatment because the venous blood pressure measuring means updates the alarm-threshold.

Further, the blood purification device variably sets the time interval to update the alarm-threshold of the venous blood pressure monitoring means, depending on the variation of the pressure measured or the predicted pressure to be measured by the venous blood pressure measuring means; and the time interval when the pressure changes radically is set shorter than when the pressure changes moderately.

Therefore, false alarms are controlled, and an abnormality of the patient undergoing a blood purification treatment or a device being used can be accurately detected because the venous blood pressure monitoring means updates the alarm-threshold at a predetermined period of time.

Further, false alarms are controlled and an abnormality of the patient undergoing the blood purification treatment and the device for the treatment can be more accurately detected because the time interval for updating of the alarm-threshold by the venous blood pressure monitoring means is shorter when the change is large than when the change is moderate.

Further, the alarm-threshold of the venous blood pressure monitoring means is updated when a predetermined operation is carried out on device applied to other types of medical treatment.

Specifically, a false alarm is controlled when the changes of the venous blood pressure are predicted to be large because the alarm-threshold is updated by the venous blood pressure monitoring means when the predetermined operation is carried out on device being applied to other types of medical treatment.

Further, the alarm-threshold updated by the venous blood pressure monitoring means includes an upper threshold value and a lower threshold value determined from the base value which is the pressure measured or the pressure predicted to be measured by the venous blood pressure measuring means. The alarm-range from the base value to the lower threshold value is smaller than the alarm-range from the base value to the upper threshold value.

Specifically, not only false alarms because of a change of the venous blood pressure, which tends to increase during blood purification treatment, are controlled, but also the detection of a small change because of such as the needle coming off from the patient is accurately carried out because the alarm-range from the base value to the lower threshold value is set smaller than the alarm-range from the base value to the upper threshold value.

DETAILED DESCRIPTION OF PREFERRED EMBODIMENTS

Figure 1:
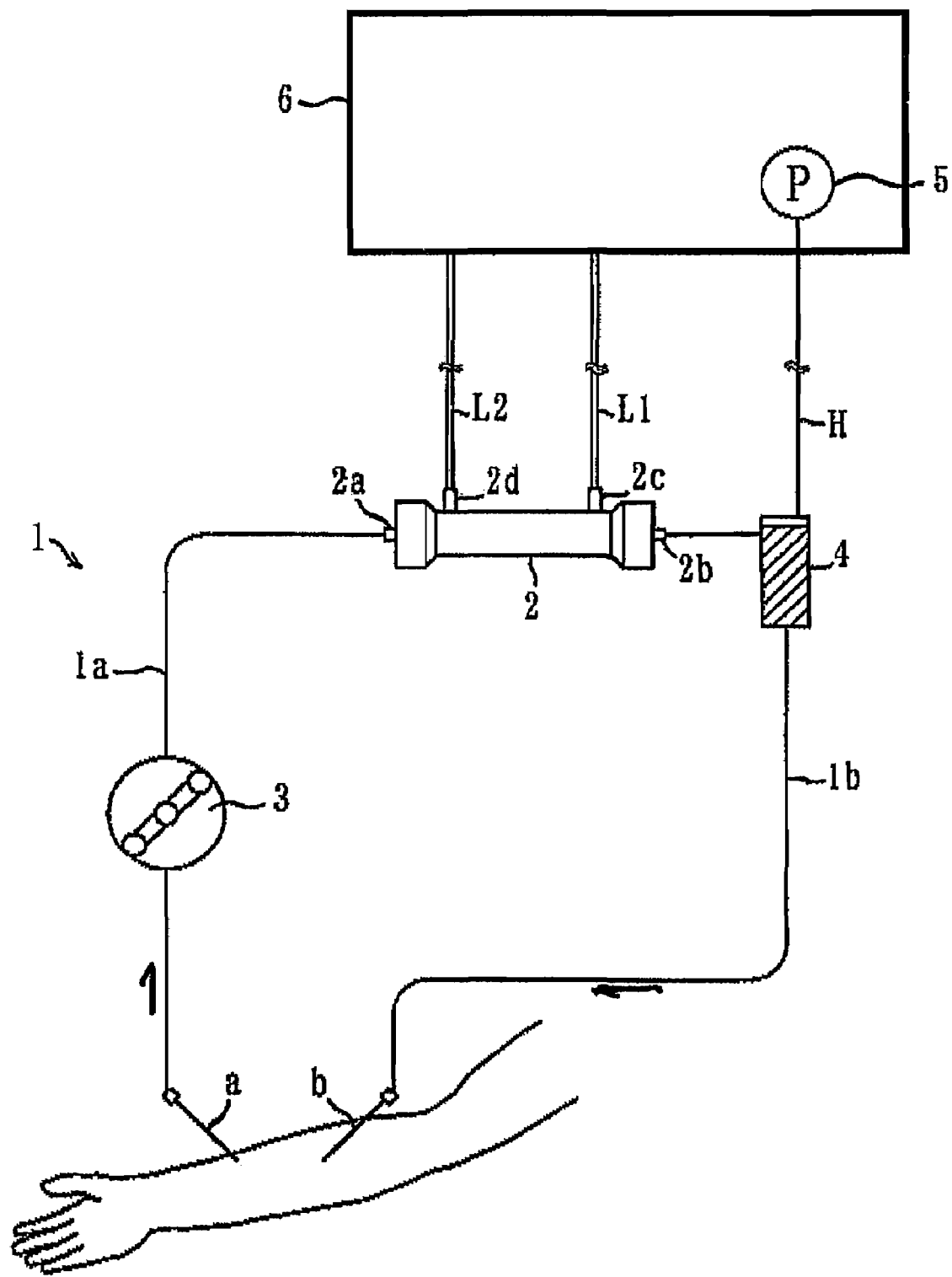
FIG. 1 is a schematic diagram of the hemodialysis equipment of embodiments 1 to 3 of the present invention described.

The embodiments of the present invention are explained using figures. The blood purification device according to embodiments 1 is a device to purify the patient's blood by extracorporeal circulation and is applied to a dialysis equipment body which is used for a dialysis treatment. The dialysis equipment includes, as shown in FIG. 1, a blood circuit attached dialysis equipment 2 as a blood purifier and dialyzer 6 supplying dialysate to dialyzer 2 and removing water. Blood circuit 1 includes mainly, as shown the same figure, arterial blood circuit 1a and venous blood circuit 1b, which are made from flexible tube and dialyzer 2 is installed between arterial blood circuit 1a and venous blood circuit 1b.

Arterial needle a is attached to the end of arterial blood circuit 1a, and roller blood pump 3 in the middle of arterial blood circuit 1a. Venous needle b is attached to the end of venous blood circuit 1b, and drip chamber 4 to remove bubbles are attached in the middle of venous blood circuit 1b and venous blood pressure measuring means 5.

When blood pump 3 is driven while arterial needle a and venous needle b are affixed to the patient, the blood of the patient flows through arterial blood circuit 1a and into dialyzer 2 which purifies the blood. The purified blood returns to the patient through venous blood circuit 1b after air bubbles are removed in drip chamber 4. Thus, the blood of the patient is purified by dialyzer 2 during extracorporeally circulating through blood circuit 1.

Several ports are located on the case of dialyzer 2; blood inlet port 2a, blood outlet port 2b, dialysate inlet port 2c and dialysate outlet port 2d. Blood inlet port 2a and blood outlet port 2b are connected to the end of arterial blood circuit 1a and venous blood circuit 1b, respectively. Dialysate inlet port 2c and dialysate outlet port 2d are connected to dialysate inlet line L1 and dialysate outlet line L2, respectively. Lines L1 and L2 extend from dialysis equipment body 6.

The dialyzer includes multiple hollow fibers. The blood flows inside of the hollow fibers and the dialysate flows between the outside surface of the hollow fibers and the inside surface of the dialyzer case. The hollow fibers include many micropores that are located in the outside and the inside surface of the hollow fiber membrane, and through which waste products in the blood are dialyzed to the dialysate.

Figure 2:
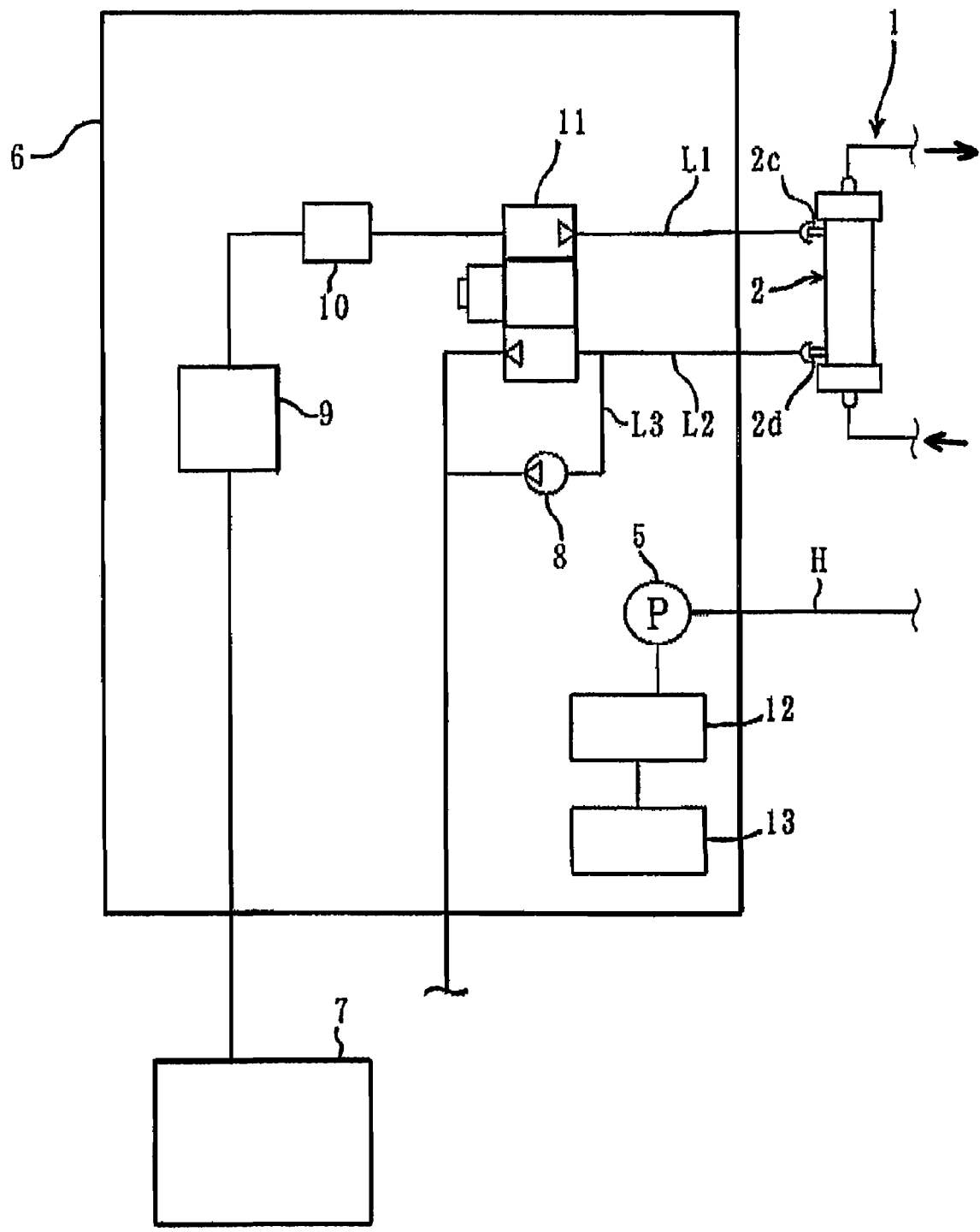
FIG. 2 is a schematic diagram of the dialysis equipment body of the hemodialysis equipment.

Further, as shown in FIG. 2, dialysis equipment body 6 includes; duplex pump 11 that is connected between dialysate inlet line L1 and dialysate outlet line L2; bypass line L3 is connected to dialysate inlet line L2 bypassing duplex pump 11; and water removal pump 8 that is connected to bypass lines L3. Additionally, one end of dialysate inlet line L1 is connected to dialyzer 2 (dialysate inlet port 2c) and the other end is connected to dialysate supplier 7 which prepares the dialysate of the predetermined concentration.

One end of dialysate outlet line L2 is connected to dialyzer 2 at dialysate outlet port 2d. The other end of dialysate outlet line L2 is connected to water fluid disposal means (not shown in Fig.). The dialysate supplied from dialysate supplier 7 passes through dialysate inlet line L1 to dialyzer 2, dialysate outlet line L2 and bypass line L3, and is let out to the water fluid disposal means. In FIG. 2, a heater 9 and a degasser 10 are both connected to dialysate inlet line L1.

Water removal pump 8 removes water from the blood of the patient flowing through dialyzer 2. When water removal pump 8 is activated, the volume of dialysate let out of dialysate outlet line L2 becomes greater than that of dialysate introduced from dialysate inlet line L1 because duplex pump 11 is quantitative; and water is removed from the blood by the difference of the inlet and outlet volume. Instead of water removal pump 8, other means (e.g. a balancing chamber) can be used to remove water from the blood of the patient.

Venous blood pressure sensor 5, a venous blood pressure measuring means, is connected to the end of monitoring tube H extended from air layer side of drip chamber 4. Venous blood pressure sensor 5 includes a sensor attached in the inside of dialysis equipment body 6 and allows real time measuring the pressure, venous blood pressure, of the patient's blood flowing in venous blood circuit 1b during a dialysis treatment.

Further, venous blood pressure monitoring means 12 is electrically connected to venous blood pressure sensor 5 and allows transferring the electric signal of venous blood pressure measured by venous blood pressure sensor 5 to venous blood pressure monitoring means 12. Venous blood pressure monitoring means 12 compares the pressure measured by venous blood pressure sensor 5 and the predetermined alarm-threshold, and if it decides that the pressure is out of the predetermined alarm-threshold range, it activates an alarm with alarming means 13. Venous blood pressure monitoring means 12, for example, is composed of a microcomputer which controls various movements and displays in the hemodialysis equipment.

Alarming means 13 let a medical worker pay attention by e.g. making a predetermined sound from a speaker, flashing an alarm lamp, and/or displaying in the display (none of them is shown in Fig.), when venous blood pressure monitoring means 12 decides that the venous blood pressure is out of the predetermined alarm-threshold range. In addition, it can be set as the device automatically ceases momentarily or in a certain period of time after the alarming means is activated.

Figure 3:
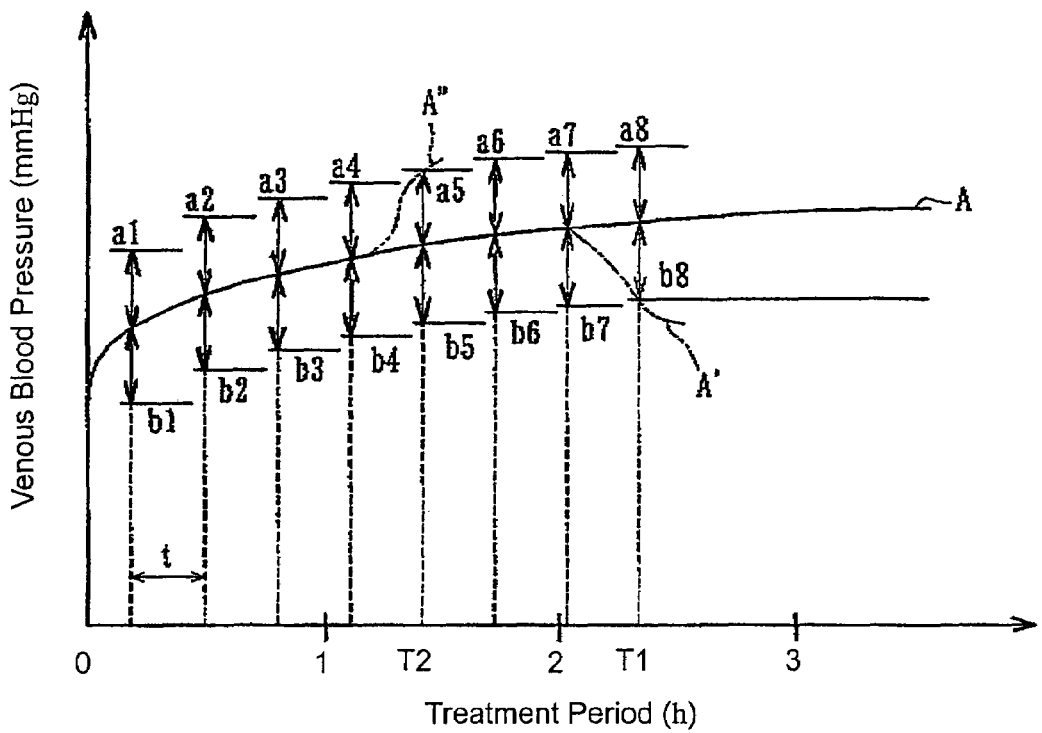
FIG. 3 is a graph which shows monitoring and controlling the venous blood pressure by the venous blood pressure monitoring means in the hemodialysis equipment of embodiment 1.

Venus blood pressure monitoring means 12 updates, as shown in FIG. 3, the alarm-threshold every predetermined time interval t (e.g. every 2 minutes), based on the pressure measured by venous blood pressure sensor 5 after blood pump 3 is activated. Specifically, as shown in the same Fig. in which the abscissa axis represents the treatment period (h) and the ordinate axis represents the venous blood pressure (mmHg) measured by venous blood pressure sensor 5, the venous blood pressure tends to gradually increase in accordance with blood concentration along with such as water removal from the blood of the patient, which is represented by graph A, and upper threshold value a1~ and lower threshold value b1~ are both updated based on the venous blood pressure measured every predetermined time interval t.

Accordingly, the difference between the venous blood pressure and the alarm-threshold can be set adequately because upper threshold value a1~ and lower threshold value b1~ as an alarm-threshold are updated from time to time every predetermined time interval. For example, as shown graph A', when venous needle b comes off from the patient or is apart from venous blood circuit 1b at time T1 and then the venous blood pressure decreases as shown in graph A' or when the venous blood pressure increases as shown in graph A" along with the patient's condition which becomes worse at time T2, the change can be detected accurately as early as possible and the medical worker can pay attention with the activated alarm.

Further, the alarm threshold range (i.e. difference between the upper threshold value and the base value or the base value and the lower threshold value) can be set as extremely narrow (as more strict to activate the alarm) because upper threshold value a1~ and lower threshold value b1~ as alarm-thresholds are updated based on the venous blood pressure, which varies from time to time, measured every predetermined period of time. For example, the change of venous blood pressure due to such as the change of the patient's condition or coming-off of venous needle b, which must be absolutely alarmed, can be accurately measured and accordingly a false alarm due to increase tendency in graph A which would occur in the traditional device, in which the alarm-threshold is not updated, can be prevented.

Further, when venous needle b comes off from the patient (as well as when venous needle b is apart from venous blood circuit 1b), nevertheless the resistance of the fluid introduced into the patient's vein becomes null, decrease of venous blood pressure will be small in many cases (e.g. decrease of such as A') because of fluid resistance with the needle and the blood circuit. Therefore the alarm-threshold between the base value and lower threshold value b1~ can be set as smaller than the alarm-threshold between the base value and upper threshold value a1~ to be able to detect surely such a small decrease of the venous blood pressure. According to this setting, coming-off venous needle b from the patient can be accurately detected to prevent activation of a false alarm along with a change of the venous blood pressure which tends to increase as shown in graph A.

Further the blood purification device according to embodiment 2, as aforementioned embodiment, is a device to purify the patient's blood by extracorporeal circulation and is applied to a dialysis equipment which is used for a dialysis treatment. The dialysis equipment mainly includes, as shown in FIG. 1 and FIG. 2, blood circuit 1 attached dialyzer 2 as a blood purifier and dialysis equipment body 6. The same element in the previous embodiment has the same sign and its detail explanation is not described here.

Venous blood pressure monitoring means 12 updates the alarm-threshold based on the pressure measured by venous blood pressure sensor 5 every predetermined time interval. The time interval is variable in accordance with variation of the pressure and the time interval when the variation is radical is set as shorter than the time interval when the variation is moderate.

Figure 4:
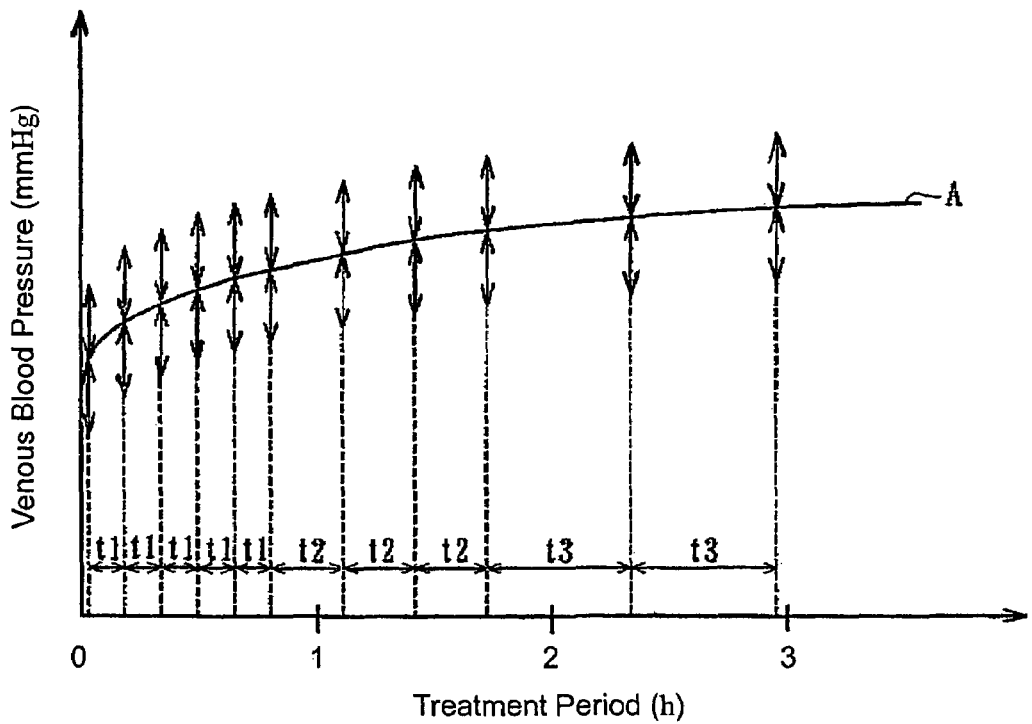
FIG. 4 is a graph which shows monitoring and controlling the venous blood pressure by the venous blood pressure monitoring means in the hemodialysis equipment of embodiment 2.

Specifically, when the pressure measured by venous blood pressure sensor 5 is as shown on graph A in FIG. 4, the time interval to update the alarm-threshold of venous blood pressure monitoring means 12 when the pressure variation is radical is set as shorter than the time interval when the pressure variation is moderate. Such variation, the pressure variation, of the venous blood pressure per time unit is calculated by such as a computer based on the venous blood pressure measured by venous blood pressure sensor 5.

For example, if a variation of the venous blood pressure per time unit is $\Delta Vp$ (venous blood pressure)/$\Delta T$ (time) and a variation of the venous blood pressure per blood flow volume (flow rate) is $\Delta Vp/(\Delta mL/min)$, the variation level, as radical or moderate, of the pressure is classified into 3 levels and, as shown in FIG. 4, the time intervals when it is radical through when it is moderate are set as t1, t2 and t3 (i.e. t1<t2<t3). Further as shown in FIG. 4, generally speaking the venous blood pressure increases extremely radically in the early stage of dialysis treatment and then its increase tends to gradually become moderate. Therefore the time interval in the early stage of dialysis treatment to update the alarm-threshold is short and then the time interval is set as longer toward its late stage.

Accordingly not only a false alarm depending on increase tendency of the measured venous blood pressure is reduced, but also such as a change of the venous blood pressure due to the change of the patient's condition, an accident in which the needle comes off from the patient or the needle is apart from the blood circuit, a clogging of the dialyzer occurs and a defect of extracorporeal circulating system occurs, can be accurately and immediately detected to activate an alarm, because when a change of the venous blood pressure is big, the alarm-threshold can be more frequently updated.

Further, instead of the aforementioned control or in parallel, it is preferable that the time intervals to update an alarm-threshold according to each period of time including when variation of the venous blood pressure is radical, moderate and almost none are automatically set (e.g. every two minute period of time when variation of the venous blood pressure is radical, every 5 minute period of time when moderate, and every 15 minute period of time when it is almost none).

Further the blood purification device according to embodiment 3, as aforementioned two embodiments, is a device to purify the patient's blood by extracorporeal circulation and is applied to a dialysis equipment which is used for a dialysis treatment. The dialysis equipment mainly includes, as shown in FIG. 1 and FIG. 2, blood circuit 1 attached dialyzer 2 as a blood purifier and dialysis equipment body 6. The same element in the previous embodiment has the same sign and its detail explanation is not described here.

Venous blood pressure monitoring means 12 is set to allow controlling update of the alarm-threshold every predetermined time interval according to the pressure measured by venous blood pressure sensor 5 and also to allow updating the alarm-threshold when a predetermined operation is carried out to provide other action for medical treatment. Such predetermined operation is carried out at time when, for example, a blood pump is activated in accordance with a programmed operation by an operator or a device, blood pump 3 is ceased, a volume of flowing blood (a flow-rate of the blood flowing in blood circuit 1) by blood pump 3 is changed, a water removal rate is changed, or a substitution fluid pump is activated and its driving rate is changed.

Figure 5:
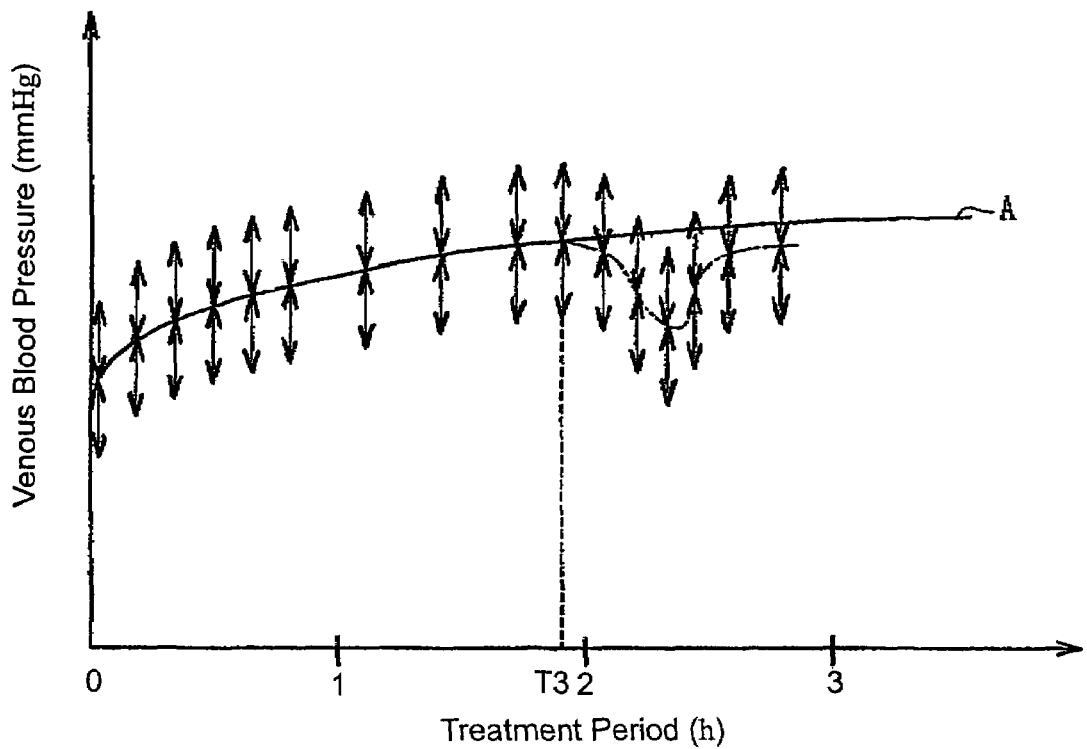
FIG. 5 is a graph which shows monitoring and controlling the venous blood pressure by the venous blood pressure monitoring means in the hemodialysis equipment of embodiment 3.
Figure 6:
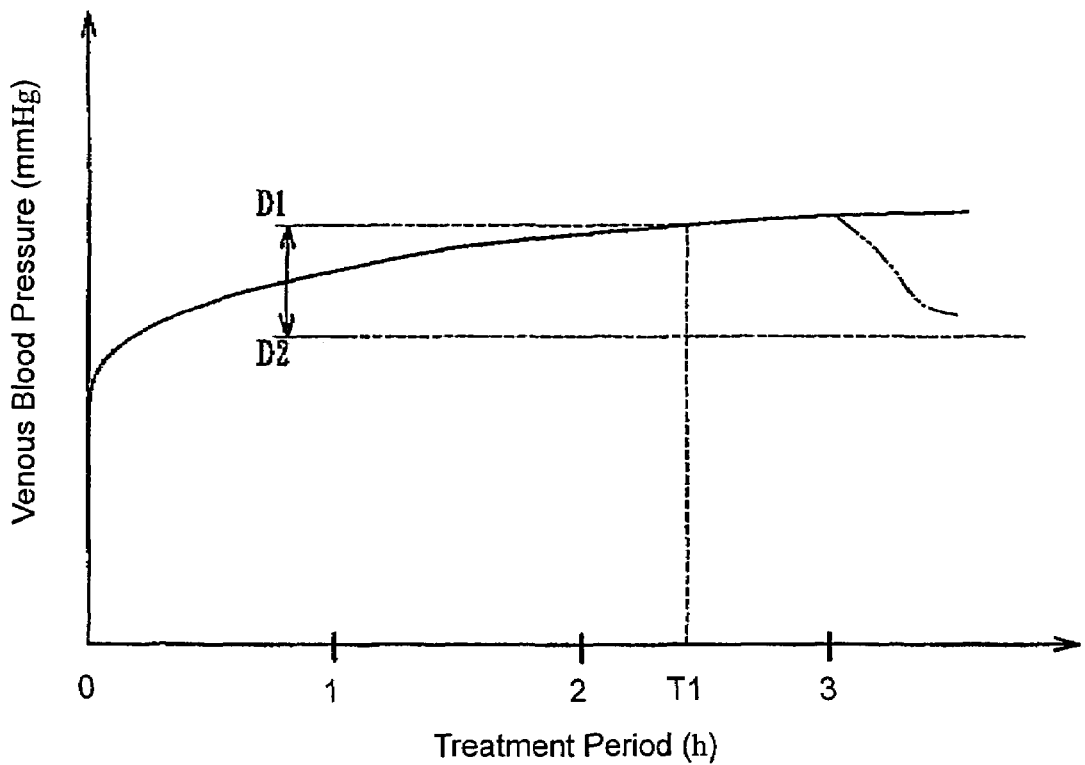
FIG. 6 is a graph which shows monitoring and controlling the venous blood pressure by the venous blood pressure monitoring means in a traditional hemodialysis equipment.

When another operation is carried out in accordance with the aforementioned operation, as shown as a dot line in FIG. 5, it is predicted that the pressure measured by venous blood pressure sensor 5 varies radically, so that, as shown in FIG. 5, an update of alarm-threshold is carried out at T3 when the operation is carried out. Therefore it is not required to activate an alarm and also an activation of false alarm at when it is predicted that the blood pressure variation becomes radical on other operation can be more accurately prevented.

Further in the present embodiment as well as embodiment 2, the time interval to update the alarm-threshold varies depending on the variation of the pressure measured by venous blood pressure sensor 5. The time interval when the variation of the pressure is radical is set as shorter than the time interval when the variation of the pressure is moderate. Accordingly, more precise monitoring can be carried out to be able to prevent a false alarming when the venous blood pressure variation is radical on other treatment. Further, an update also may be carried out when a reset is executed on alarming with alarming means 13.

In embodiments 1 through 3, the timing to update the alarm-threshold by venous blood pressure monitoring means 12 is every predetermined time including a preset period of time and any preset time (such as time when a predetermined operation on the device is carried out, time when the predicted pressure variation occurs, and time depending on variation of the pressure to be measured).

The present invention is not limited to the present embodiments. For example, the alarm-threshold is set only for the lower threshold value and the upper threshold value can be set as a fixed constant value employed during dialysis treatment. Specifically, generally speaking, the venous blood pressure is lowered when venous needle b in venous blood circuit comes off from the patient or is apart from venous blood circuit so that the lower threshold value is updated every predetermined period of time and the upper threshold value can be fixed. Accordingly, controlling system to monitor the needle in venous blood circuit coming off from the patient or being apart from the venous blood circuit by the venous blood pressure monitoring means can be simplified.

According to the present embodiment, the venous blood pressure monitoring means compares the pressure measured as the base value by the venous blood pressure measuring means with the predetermined alarm-threshold, but the pressure which is predicted to be measured by the venous blood pressure measuring means can be set as the base value. Such prediction is carried out by calculation based on condition of the patient's blood flowing in the venous blood circuit. For example, the venous blood pressure can be predicted from the blood concentration (i.e. hematocrit value (Ht), albumin value and/or total protein value).

Further, the pressure which is predicted to be measured by the venous blood pressure measuring means can be obtained by using parameters relating to blood dilution (i.e. a total amount of water removed from the blood or a unit amount of water removed, a total amount of an injected saline or substitution fluid or a unit amount of them). Further it is preferred that an adjustment to eliminate an error and to increase accuracy of the predicted value is performed with understanding the error between the variation of the venous blood pressure (tendency) and the predicted pressure which occurred in the past treatment.

Further, according to the present embodiment, dialysis equipment body 6 is a dialysis monitoring device having no inside dialysate supplier mechanism, but the present invention can be applied to a personal dialysis device including a inside dialysate supplier mechanism. In addition, the hemodialysis treatment of the present embodiments, the present invention can be applied to other blood purification device including such as a hemofiltration treatment and a hemodiafiltration treatment.

Further, if a blood purification device has the venous blood pressure monitoring means which can update the alarm-threshold every predetermined period of time, the present invention can be applied to which has a different appearance or another function.

We claim:

1. A blood purification device comprising:
   a blood circuit having an arterial blood circuit and a venous blood circuit to circulate extracorporeally blood collected from the patient;
   a blood pump provided for said arterial blood circuit;
   a blood purification means, connected between said arterial blood circuit and said venous blood circuit, for purifying the blood flowing in said blood circuit;
   a venous blood pressure measuring means for measuring the pressure of a patient's blood flowing in said venous blood circuit;
   a venous blood pressure monitoring means for activating an alarm by comparing a predetermined alarm-threshold pressure with pressure measured or pressure predicted to be measured, as a base value, by the venous blood pressure measuring means; and
   a device that is configured to determine a time interval to update the alarm-threshold pressure of said venous blood pressure monitoring means by calculating a level of variation in the pressure measured by said venous blood pressure measuring means,
   wherein said venous blood pressure monitoring means updates said predetermined alarm-threshold pressure after said time interval.

2. The blood purification device according to claim 1, wherein said time interval is set shorter when the variation is large than when the variation is moderate.

3. The blood purification device according to claim 2, wherein said venous blood pressure monitoring means is configured to update the predetermined alarm-threshold pressure when a predetermined operation to be carried out that changes the operation of the device occurs.

4. The blood purification device according to claim 2, wherein the predetermined alarm-threshold pressure, which is updated by said venous blood pressure monitoring means, includes an upper threshold value and a lower threshold value, wherein the pressure measured or the pressure predicted to be measured by said venous blood pressure measuring is set as a base value, and wherein a range of the alarm-threshold from the base value to the lower threshold value is smaller than a range of the alarm-threshold from the base value to the upper threshold value.

5. The blood purification device according to claim 2, wherein the time interval is selected as one of three predetermined time intervals t1, t2, t3, wherein t1<t2<t3.

6. The blood purification device according to claim 5, wherein the predetermined time interval t1 is two minutes, the predetermined time interval t2 is five minutes, and the predetermined time interval t3 is 15 minutes.

7. The blood purification device according to claim 1, wherein said venous blood pressure monitoring means is configured to update the predetermined alarm-threshold pressure when a predetermined operation to be carried out that changes the operation of the device occurs.

8. The blood purification device according to claim 7, wherein the predetermined alarm-threshold pressure, which is updated by said venous blood pressure monitoring means, includes an upper threshold value and a lower threshold value, wherein the pressure measured or the pressure predicted to be measured by said venous blood pressure measuring means is set as a base value, and wherein a range of the alarm-threshold from the base value to the lower threshold value is smaller than a range of the alarm-threshold from the base value to the upper threshold value.

9. The blood purification device according to claim 1, wherein the predetermined alarm-threshold pressure, which is updated by said venous blood pressure monitoring means, includes an upper threshold value and a lower threshold value, wherein the pressure measured or the pressure predicted to be measured by said venous blood pressure measuring is set as a base value, and wherein a range of the alarm-threshold from the base value to the lower threshold value is smaller than a range of the alarm-threshold from the base value to the upper threshold value.

10. The blood purification device according to claim 1, wherein said venous blood pressure monitoring means updates said predetermined alarm-threshold based on pressure measured or pressure predicted to be measured.

11. The blood purification device according to claim 1, wherein said venous blood pressure monitoring means updates said predetermined alarm-threshold pressure based on a measured pressure in said venous blood circuit.

* * * * *